(12) United States Patent
Chen et al.

(10) Patent No.: US 6,534,004 B2
(45) Date of Patent: Mar. 18, 2003

(54) PROCESSING OF IMPLANTABLE ANIMAL TISSUES FOR DRY STORAGE

(75) Inventors: Ji-Feng Chen, Lakewood, OH (US); Kent Wika, Mounds View, MN (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/752,313

(22) Filed: Dec. 28, 2000

(65) Prior Publication Data

US 2001/0023372 A1 Sep. 20, 2001

Related U.S. Application Data

(63) Continuation-in-part of application No. 09/078,970, filed on May 14, 1998, now abandoned.

(51) Int. Cl.[7] .................................................. B01J 19/00
(52) U.S. Cl. ................................. 422/40; 422/1; 435/1; 435/240.2; 435/240.3; 623/15
(58) Field of Search ...................... 435/1, 240.2, 240.3; 623/15, 1, 28; 422/40

(56) References Cited

U.S. PATENT DOCUMENTS 5,336,616 A * 8/1994 Livesay et al. .......... 435/240.2
6,312,474 B1 * 11/2001 Francis et al. ........... 623/23.72

* cited by examiner

*Primary Examiner*—Krisanne Thornton
(74) *Attorney, Agent, or Firm*—Calfee, Halter & Griswold LLP

(57) ABSTRACT

A method that allows for dry storage of bioprosthetic devices comprising a tissue component is provided. The method comprises the steps of providing a device comprising a chemically cross-linked animal tissue component; treating the tissue component with an aqueous solution comprising a biocompatible, water soluble, organic molecule comprising a plurality of carbon atoms and a plurality of hydroxyl groups for a time sufficient to allow equilibration between the fluids in the interstices of the tissue component and the aqueous solution; and then sterilizing the treated tissue component using a sterilizing gas or ionizing radiation. The present invention also relates to an implantable tissue component that can be stored dry. The tissue component is chemically-fixed and comprises within the interstices thereof a dimensional stabilizer selected from the group consisting of a polyhydric alcohol and derivatives thereof, a water soluble carbohydrate, and a water soluble gum. The tissue component is disposed within the chamber of a package, the chamber being defined by one or more members formed from a material that is resistant to penetration by micro-organisms, particularly bacteria and fungi. The chamber and tissue component are sterile and essentially free of an aldehyde solution. Except for the liquids contained within the tissue component, the chamber is also essentially free of liquid.

28 Claims, 2 Drawing Sheets

PROCESSING OF IMPLANTABLE ANIMAL TISSUES FOR DRY STORAGE

CROSS-REFERENCE TO RELATED APPLICATIONS

This application is a Continuation-in Part of, and claims priority from the U.S. application Ser. No. 09/078,970, filed May 14, 1998 now abandoned.

BACKGROUND OF THE INVENTION

A number of implantable bioprosthetic devices are currently being used for treating patients with cardiovascular diseases and defects. Such implantable devices are useful for replacing diseased, damaged, or congenitally malformed components of the patient's cardiovascular system. Thus, damaged or diseased heart valves have been replaced with chemically-fixed, bioprosthetic heart valves prepared from tissues of porcine or bovine origin. Similarly, regions of damaged or diseased blood vessels may also be replaced with bioprosthetic vessels prepared from bovine tissues. In addition, patches made from bovine pericardium may be used for various types of tissue repair.

Typically, the animal tissues used to form implantable devices or to repair damaged tissues are chemically cross-linked with agents such as glutaraldehyde, especially those animal tissue components that come into direct contact with the patient's blood. Such treatment is necessary to prevent rejection of the implanted bioprosthetic device by the recipient. Such treatment also stabilizes the protein components of the animal tissue components of the device making them more resistant to degradation by proteolytic enzymes.

To prevent transmission of disease causing micro-organisms to the patient, it is necessary that the implantable tissue components and the bioprosthetic devices made therefrom be sterilized and stored in a sterile condition prior to use. Currently, bioprosthetic devices are sterilized by immersion in formaldehyde. The sterilized devices are then stored in a dilute aqueous solution containing formaldehyde and/or glutaraldehyde to maintain the tissue components in a hydrated state and to kill microbes. Because formaldehyde and glutaraldehyde are both irritants and suspected carcinogens, the bioprosthetic devices that are stored in solutions containing these agents must be extensively rinsed prior to use to insure that these noxious chemicals are not transferred to the patient. To maintain the sterility of the bioprosthetic device, this rinsing procedure is performed under sterile conditions in the operating room. Thus, the efficacy of rinsing is limited by the operating room conditions. Moreover, the solutions containing such aldehydes pose an environmental hazard to the operating room personnel who are exposed to these chemicals.

Attempts have been made to develop a bioprosthetic devices that can be stored dry. One attempt involves a dehydration process which involves immersing the device into chemical solutions, such as an ethyl alcohol solution, that remove a substantial amount of water from the bioprosthetic tissue component. Such dehydration processes significantly reduce the overall dimensions of the tissue component. Unfortunately, tissue components subject to this dehydration process cannot be successfully rehydrated and returned to substantially their original dimensions. As a result, bioprosthetic devices comprising tissue components that have undergone such dehydration process are not good candidates for implantation.

Accordingly, it is desirable to have new methods for preparing implantable bioprosthetic devices that are suitable for dry storage. A method that allows for controlled rinsing of the chemically cross-linked tissue components and removal of residual unreacted cross-linking agent in an environment outside of the operating room is desirable. A method that provides tissue components that are capable of being restored to substantially their original dimensions following dry storage is especially desirable.

SUMMARY OF THE INVENTION

In accordance with the present invention, a method that allows for dry storage of bioprosthetic devices comprising a tissue component is provided. In one embodiment, the method comprises the steps of providing a device comprising a chemically cross-linked animal tissue component; treating the tissue component with an aqueous solution comprising a biocompatible, water soluble, organic molecule comprising a plurality of carbon atoms and a plurality of hydroxyl groups, hereinafter referred to as a "dimensional stabilizer," for a time sufficient to allow equilibration between the fluids in the interstices of the tissue component and the aqueous solution; and then storing the treated tissue component in a sealable container that is essentially free of liquid. In another embodiment, the tissue component is sterilized using a sterilizing gas or ionizing radiation either prior to or after placement in the storage container. The advantages to dry storage of implantable tissue components include the reduced size, volume and weight of the product as compared to implantable tissue stored in a fluid medium in glass or plastic containers, and elimination of noxious fluids associated with storage of tissue components in aldehyde solutions.

The present invention also relates to an implantable tissue component that can be stored dry. The tissue component and comprises within the interstices thereof a dimensional stabilizer selected from the group consisting of a polyhydric alcohol and derivatives thereof, a water soluble carbohydrate, and a water soluble gum. In another embodiment, the tissue component is chemically-fixed. The tissue component is disposed within the chamber of a package, the chamber being defined by one or more members formed from a material that is resistant to penetration by micro-organisms, particularly bacteria and fungi. Preferably, at least a portion of one or more of the members is gas-permeable. The chamber and tissue component are sterile and essentially free of an aldehyde solution. Except for the liquids contained within the interstices of the tissue component, the chamber is also essentially free of liquid.

The present invention further relates to a method of preparing a bioprosthetic device comprising a tissue component for implantation into a patient. The method comprises obtaining a bioprosthetic device comprising a tissue component that is chemically-fixed and comprises within the interstices thereof a dimensional stabilizer selected from the group consisting of a polyhydric alcohol and derivatives thereof, a water soluble carbohydrate, and a water soluble gum; and rehydrating the tissue component in an aqueous solution.

DETAILED DESCRIPTION OF THE INVENTION

Figure 1:
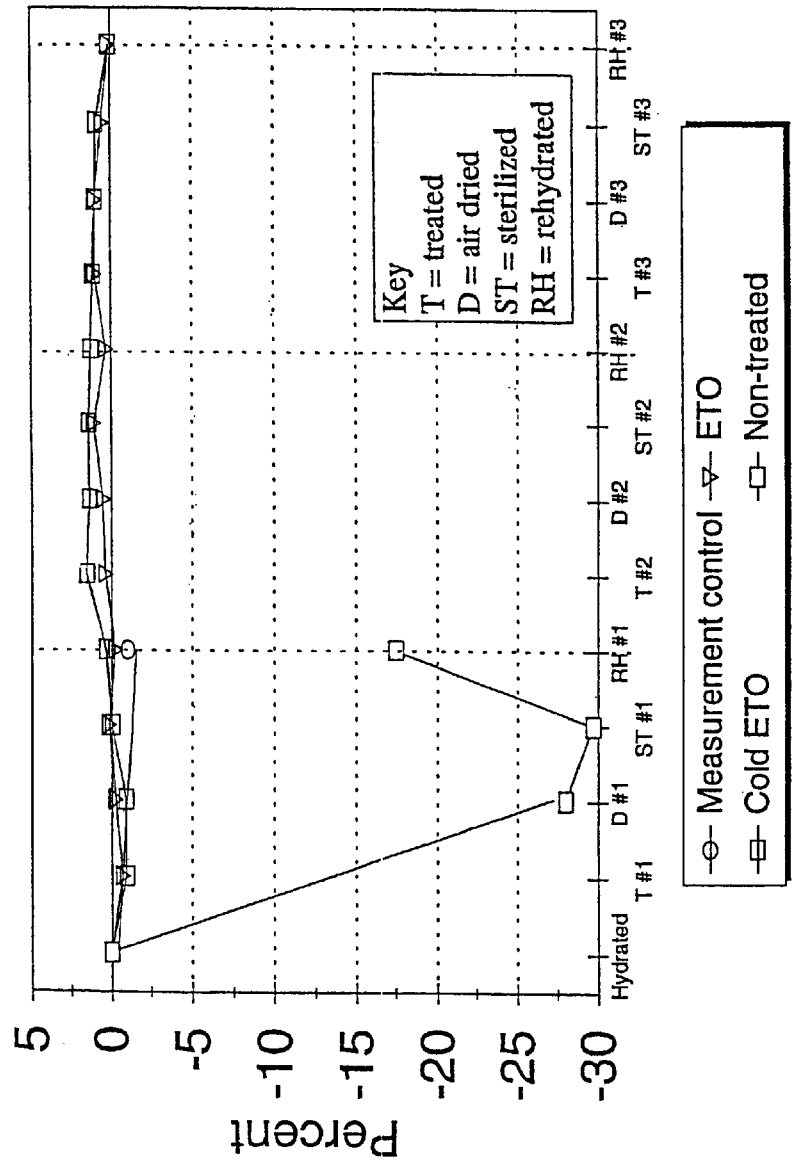
FIG. 1 is a graph depicting the change in dimensional size of non-treated and treated bovine pericardium that has undergone one or more cycles of air-drying, ethylene oxide sterilization, and rehydration.

In accordance with the present invention a method of preparing an animal tissue component, more particularly an implantable tissue component, for dry storage is provided. As used herein a tissue component means tissues that are dissected from an animal such as, for example, muscular tissues, connective tissues, or epithelial tissues, or combinations thereof, and tissues or tissue precursors that are formed in animal cell cultures. Such implantable tissue components include, but are not limited to, heart valves and pericardium obtained from non-human animals, such as for example porcine or bovine animals.

Preferably, the tissue component is fixed. As used herein a "fixed" tissue component is one in which the proteins thereof have reduced solubility, antigenicity, and biodegrading properties as compared to the proteins in the native tissue component. Preferably, the tissue component is fixed by cross-linking the amine groups of the proteins of the tissue component with an aldehyde. The aldehydes conventionally used for this purpose include glutaraldehyde or formaldehyde. The particular conditions and apparatus used to fix tissues are known in the art. Preferably, the fixed tissue component is thoroughly rinsed prior to processing to substantially reduce the amount of unreacted fixative within the tissue component. The number of rinses needed to achieve thorough rinsing is within the skill of the art. Thereafter, the fixed tissue component is processed immediately or stored in an aqueous environment until processing to prevent drying out and shrinkage of the fixed tissue component, i.e. to keep the tissue component in a "wet" or hydrated state.

In accordance with the present invention, the tissue component is treated with an aqueous solution comprising at least one non-volatile, biocompatible, dimensional stabilizer at a concentration and temperature and for a time sufficient to allow an equilibrium to be reached between the fluids in the interstices of the tissue component and the aqueous solution. As used herein, a dimensional stabilizer is an organic molecule that is hydrophilic and that comprises a plurality of carbon atoms and a plurality of hydroxyl groups, wherein each of the plurality of hydroxyl groups are attached to a carbon atom. Suitable dimensional stabilizers are, for example, water soluble polyhydric alcohols such as glycerol, ethylene glycol, polyethylene glycols, propylene glycol, butylene glycol, sorbitol, mannitol, and pentaerythritol; water soluble carbohydrates such as ribose, maltose, sucrose, fructose, dextrose, dextran, cellulose, and methyl cellulose; pectin; derivatives of glycerol such as for example, glycerol bori-borate and glycerol borate akerite glycerin alternative; and water soluble gums. Because of their favorable hygroscopicity, good solubility in water, low degree of volatility, and biocompatibility, the preferred dimensional stabilizers are water-soluble polyhydric alcohols or derivatives thereof. More preferably, the aqueous solution comprises glycerol or a derivative thereof, most preferably glycerol. Preferably, the aqueous solution comprises from about 30% to about 95%, more preferably from about 50% to about 90%, most preferably from about 50% to about 70% of the dimensional stabilizer.

The tissue component is contacted with the aqueous treatment solution for a time and at a temperature sufficient to permit the treatment solution to penetrate into the interstices of the tissue component and achieve an equilibrium between the treatment solution and the fluids in the interstices of the tissue component. The time needed to achieve such equilibrium is directly related to the thickness of the tissue component and to the concentration of the dimensional stabilizer in the solution, and inversely related to the ratio between the volumes of the treatment solution and the volume of the tissue component, and to the rate of mixing of the treatment solution. Preferably, a tissue component having a thickness of from about 0.05 mm to about 2 mm is contacted with the aqueous treatment solution for at least 120 minutes at a temperature of from about 15° C. to about 25° C.

The tissue component is contacted with the aqueous treatment solution by standard methods such as by immersion in the solution. Preferably, the volume of the aqueous treatment solution is at least 2 times, more preferably 50 times, most preferably 100 times, the volume of the tissue component that is brought into contact with the solution. The tissue component may be treated with the aqueous treatment solution prior to the time it is fashioned into the implantable bioprosthetic device, after it is fashioned into the bioprosthetic device, or at both stages in the manufacture of the bioprosthetic device. Thus, bovine pericardium may be treated with the aqueous treatment solution prior to the time it is formed into a heart valve, vascular graft or pericardial patch or after it is formed into a heart valve, vascular graft or pericardial patch, or both.

Optionally, the tissue component is exposed to ambient air at standard room temperature and humidity (at a temperature from about 15° C. to about 25° C., and relative humidity from about 10% to about 30%) following treatment with the aqueous treatment solution. The tissue component is air dried for a time sufficient to increase the viscosity of the dimensional stabilizer in the solution entrapped within the interstices of the tissue component such that the treated tissue component is essentially free from excess aqueous treatment solution. Preferably, the drying is performed in a clean room or in a laminar flow bench at ambient room conditions and at a relative humidity of from about 10% to about 30% for at least 4 hours. Increasing the viscosity as described above permits the dimensional stabilizer to remain within the interstices during subsequent processing of the tissue component or the bioprosthetic device comprising the tissue component, i.e., during sterilization and storage. Removal of excess aqueous treatment solution enhances packaging and handling of the tissue component.

The treated tissue component or the bioprosthetic device comprising the tissue component is then stored in an environment essentially free of liquid for later processing or implantation. An environment, container or package that is "essentially free of liquid" as described herein means a non-fluid environment in which the presence of water or other liquids is limited to the content of such liquids in the ambient air (as more precisely defined by the relative humidity), and the content of liquid contained within a treated tissue component disposed within a container or package. Preferably, the tissue component or the bioprosthetic device made therefrom is placed into the chamber of a micro-organism resistant package. The chamber is defined by the inner surface of one or more members. The packaged treated tissue component may then be sterilized by a gas sterilization process or by exposure to ionizing radiation. To ensure that the chamber remains sterile following sterilization, the package members are formed from a material that is impenetrable to micro-organisms such as bacteria and fungi. Thus, the material used to form the chamber-defining members preferably has pores with a diameter of less than 0.2 μm. Preferably, a portion of the member or members defining the chamber is formed from a polymeric material that is gas permeable. After the tissue component is placed in the chamber, the chamber is sealed and the tissue component or bioprosthetic device contained therein is sterilized, preferably by exposure to ionizing radiation or to a sterilizing gas, more preferably by exposure to ethylene oxide.

Sterilization by exposure to ionizing radiation or sterilizing gas, particularly by exposure to ethylene oxide, is within the skill of the art. Examples of conventional procedures for sterilization by exposure to ethylene oxide involve exposure to 10% ethylene oxide and 90% hydrochlorofluorocarbon at a chamber pressure of 8 to 10 psig at a temperature of 38° C. for 24 hours or at a temperature of 54–57° C. for 130 minutes.

The resulting product is a substantially sterile implantable tissue component or bioprosthetic device suitable for dry storage. The sterile tissue components prepared in accordance with the present method are especially well-suited for implantation into patients with cardiovascular diseases. As used herein, patient means any mammal, such as for example humans, dogs, cats, horses, and non-human primates. Prior to use, the tissue component or bioprosthetic device made therefrom is removed from the package, and the tissue component rehydrated by exposure to an aqueous solution, preferably a sterile aqueous solution. More preferably, the tissue component is rehydrated by multiple soakings in a sterile solution such as, for example, physiologic saline. The sterilized treated tissue component may be subjected to multiple cycles of treatment with dimensional stabilizer, packaging, storage, and rehydration.

The present method eliminates the need to sterilize bioprosthetic devices or bioprosthetic materials made from a chemically cross-linked tissue component in an aldehyde containing solution. The present method also eliminates the need to store such devices and materials in an aldehyde-containing solution. The present method permits controlled rinsing of chemically cross-linked tissue components at the site of cross-linking rather than the operating room. Accordingly, the present method minimizes, if not eliminates, the possibility of introducing aldehydes into the blood stream of the patient. The present method also avoids the problems associated with exposing the manufacturing or operating room personnel to the fumes given off by the aldehyde-containing solutions. The present method may also reduce the amount of time spent in the operating room preparing the medical devices that comprise a tissue component for implantation.

Moreover, the present method provides a tissue component that has dimensional stability, i.e., the method of treatment described herein dimensionally stabilizes the tissue component. As a result, a tissue component treated in accordance with the present methods can be returned to a size that is at least 90%, preferably at least about 95%, more preferably at least about 98% of its original hydrated size following dry storage for about 24 hours and rehydration in physiologic saline for about 10 minutes. As a result, the tissue components prepared in accordance with the present method are well-suited for use in an implantable bioprosthetic device, particularly a bioprosthetic device that is implanted into the cardiovascular system of a patient.

The following examples are for purposes of illustration only and are not intended to limit the scope of the invention as defined in the claims which are appended hereto.

EXAMPLE 1

Single Cycle Dimensional Stabilization of Bovine Pericardium.

Bovine pericardium obtained from a local packing house was cross linked by storing in a 0.1 M phosphate buffered solution, pH 7.43–7.46, containing 0.45% glutaraldehyde for more than 24 hours. Following exhaustive rinsing in sterile physiologic saline, the pericardium was placed in 4% formaldehyde in 0.1 M phosphate, pH 7.0 and stored at room temperature. Twenty circular disks having a diameter of 0.5 inches and a thickness of about 500 $\mu$m were cut from the chemically cross-linked sheet of bovine pericardium using a stainless steel die. After being cut, the disks were stored for at least 24 hours in the same 4% formaldehyde solution to allow residual strains from cutting to be released. The discs were labeled with a permanent marker so that the diameter of each disk could be determined and repeatedly measured following each step of the treatment. For baseline data, the diameters of all 20 disks were measured and recorded. All measurements were made with a scaled microscope.

Ten of the disks (hereinafter referred to as the test disks) were immersed in an aqueous solution containing 57% by volume of glycerol. The volume of the aqueous treatment solution was 50 times the volume of the test disks. After 2 hours of treatment at room temperature, the test disks were removed from the aqueous treatment solution and air dried in a laminar hood at room temperature and at a relative humidity of 10% to 30% for 24 hours. The test disks were divided into two equal groups of 5 disks, which were then placed into separate gas sterilization packages and sterilized by exposure to ethylene oxide. One group was sterilized by ethylene oxide at 38° C. ("cold ETO group"), while the other group was sterilized by ethylene oxide at 54–57° C. ("ETO group").

A third group of five circular disks ("non-treated group") served as controls for the treatment process. The disks in this non-treated group were put in water lacking a dimensional stabilizer for 2 hours at room temperature and then air dried in a laminar hood at room temperature and at a relative humidity of 10% to 30% for 24 hours. The disks in the non-treated group were also sterilized by exposure to ethylene oxide at 54–57° C.

A fourth group of five disks ("measurement control group") served as controls for the measurement method. The disks in the measurement control group were stored in physiologic saline for 2 weeks while the other groups were being processed.

After sterilization in ethylene oxide, the test disks and the control disks in the non-treated group were subjected to three rinse cycles in physiologic saline at room temperature. Each rinse cycle was for 10 minutes. After each step in the process, the marked diameter of each disk was measured. The dimensions were converted to percent of initial hydrated size and are shown in FIG. 1.

As shown in FIG. 1, treatment of the test disks with an aqueous treatment solution comprising 57% v/v of the dimensional stabilizer glycerol significantly limited shrinkage of the test disks during the air drying step as compared to the disks in the non-treated group. The initial size, i.e., diameter, of the test disks decreased by less than 2% during the air drying step which is just over the 1% variability observed for the measurement control group. In contrast, the diameter of the disks in the non-treated control group decreased by more than 25% during the air drying step. For the test disks in both the cold ETO group and the ETO group, a further diameter decrease of about 1% was observed after gas sterilization. Upon rehydration with physiologic saline, the diameter of the test disks in both test groups returned to 98.7% of the original value. In contrast, the diameter of the non-treated controls increased to less than 85% of the original diameter after rehydration. In addition to exhibiting dimensional instability, the non-treated controls also became rigid and brittle. The changes observed in the non-treated controls could not be reversed.

These results show that treatment with an aqueous treatment solution comprising a dimensional stabilizer is useful for preparing biological materials, particularly the biological materials used to make implantable cardiac valves, for gas sterilization and for dry storage. These results also demonstrate that the changes observed in tissue components that have been subjected to dry storage can be reversed by rehydration when such tissue components are treated in accordance with the present method.

In-plane Dimension Change The extent of dimensional change induced by various dry storage processing methods was evaluated for bovine pericardium. The term "dimensional change" means the change in the measured value of either the diameter or the thickness of a tissue sample, or the change in the shape of a tissue sample, after various steps of processing.

Disks cut from cross-linked bovine pericardium treated with an aqueous solution containing a dimensional stabilizer as described above were compared to discs cut from cross-linked bovine pericardium processed either by lyophilization, or exposure to acetone or ethanol. After processing with either dimensional stabilizer, lyophilization, acetone or ethanol, all of the discs were air dried and then rehydrated with saline.

Dimensional measurements were taken for each disk immediately after processing (hydrated state), and after rehydration with saline (rehydrated state). Opposite ends of a diameter line were marked with sutures on each disk to serve as reference points for measuring dimensional changes. Dimensions were measured using a toolmakers microscope and the percent change from the hydrated size was calculated. Dimensional shape was assess for each disk immediately after processing (hydrated shape), after drying (dehydrated shape), and after rehydration with saline (rehydrated shape).

Table 1 shows the results for in-plane dimensional changes for cross-linked bovine pericardium with the various treatment methods. Lyophilization, acetone exposure, and ethanol exposure all induce permanent dimensional changes in bovine pericardium, as evidenced by the altered rehydrated shapes of tissue discs processed by these methods. For the dimensional stabilization method described herein, no changes were observed in the shape during any step of the processing (including the dehydrated step) or in the measured size from hydrated to rehydrated.

TABLE 1

Cross-linked Bovine Pericardium In-plane Dimensional Change

| Treatment | Hydrated Shape | Dehydrated Shape | Rehydrated Shape | Percent Change from Hydrated |
|---|---|---|---|---|
| Acetone | Circular | Curled | Ovoid | −0.46 ± 2.11% |
| Ethanol | Circular | Curled | Ovoid | −7.36 ± 6.95% |
| Lyophilization | Circular | Curled | Irregular, not flat | not measurable |
| Dimensional Stabilization | Circular | Circular | Circular | −0.58 ± 0.44% |

Thickness Change

Rectangular specimens of cross-linked bovine pericardium processed with dimensional stabilizer as described above, and discs cut from cross-linked bovine pericardium processed either by lyophilization, or exposure to acetone or ethanol were evaluated for effect of processing on tissue thickness. A 3 mm long region was marked on the edge of each specimen where measurements would be made. Measurements were made at 40×magnification using a Bioquant morphometric analysis system. The average thickness within the marked region was calculated by dividing the area of the region by its length. Percent change values from the hydrated state were calculated for the dehydrated and rehydrated states.

Table 2 shows the results of the thickness measurements for ethanol, acetone, and dimensional stabilization processing methods. With all three treatments, the materials became thinner in the dehydrated state. However, upon rehydration, the specimens which were treated with the dimensional stabilization processing method returned to their original thickness values. The materials that were treated by ethanol or acetone experienced permanent dimensional changes remaining significantly thinner than their original sizes.

TABLE 2

Cross-linked Bovine Pericardium Thickness Change

| | Percent Change from Hydrated | |
| Treatment | Dehydrated | Rehydrated |
|---|---|---|
| Acetone | −50.12 ± 5.86% | −14.88 ± 6.93% |
| Ethanol | −64.88 ± 5.55% | −18.85 ± 9.25% |
| Dimensional Stabilization | −23.73 ± 9.13% | −0.76 ± 6.29% |

EXAMPLE 2

Single Cycle Dimensional Stabilization of Bovine Dura Mater

In-plane Dimension Change

The extent of dimensional change induced by various dry storage processing methods was evaluated for dura mater.

Disks cut from fresh dura mater tissue treated with an aqueous solution containing a dimensional stabilizer as described in Example 1 above were compared to discs cut from fresh dura mater processed either by lyophilization, or exposure to acetone or ethanol. After processing with either dimensional stabilizer, lyophilization, acetone or ethanol, all of the discs were air dried and then rehydrated with saline. Dimensional measurements were taken for each disk immediately after processing (hydrated state), and after rehydration with saline (rehydrated state). Opposite ends of a diameter line were marked with sutures on each disk to serve as reference points for measuring dimensional changes. Dimensions were measured using a toolmakers microscope and the percent change from the hydrated size was calculated. Dimensional shape was assess for each disk immediately after processing (hydrated shape), after drying (dehydrated shape), and after rehydration with saline (rehydrated shape).

Table 3 shows the results for in-plane dimensional changes for dura mater with the various processing methods. Lyophilization, acetone exposure, and ethanol exposure all induce permanent dimensional changes in dura mater, as evidenced by the altered rehydrated shapes of tissue discs processed by these methods. For the dimensional stabilization method described herein, no changes were observed in the shape during any step of the processing (including the dehydrated step) or in the measured size from hydrated to rehydrated.

TABLE 3

Dura Mater In-plane Dimensional Change

| Treatment | Hydrated Shape | Dehydrated Shape | Rehydrated Shape | Percent Change from Hydrated |
|---|---|---|---|---|
| Acetone | Circular | Curled | Ovoid | −0.07 ± 0.13% |
| Ethanol | Circular | Curled | Ovoid | −0.85 ± 0.07% |
| Dimensional Stabilization | Circular | Circular | Circular | −0.25 ± 0.75% |

EXAMPLE 3

Multiple Cycle Dimensional Stabilization of Bovine Pericardium

Test disks made from bovine pericardium were treated as described above in example 1 except that each test disk was subjected to two additional rounds of processing. Each round of processing involved immersion in an aqueous solution containing 57% glycerol, air drying, ethylene oxide sterilization, and rehydration in physiologic saline under conditions as described in Example 1. As shown in FIG. 1, the dimensions of the test disks did not vary by more than 2% of their original hydrated size following each round of processing. After three rounds of processing, the test disks felt as pliable as the pericardium in its initial hydrated state. The test disks were also capable of being sutured after three rounds of processing.

EXAMPLE 4

Dimensional Stabilization of Bioprosthetic Valved Conduit

A cross-linked bovine Hancock 22 mm porcine bioprosthetic valved conduit made by Medtronic Inc. was treated in an aqueous treatment solution comprising 57% glycerol as described in example 1. The valved conduit, which had been subjected to conventional hydrated processing and storage in 0.2% stabilized glutaraldehyde, was tested in an in vitro mock circulatory loop before treatment with the aqueous glycerol solution and after treatment with the aqueous glycerol solution.

The test involves placing the valved conduit into the inflow port of a single chamber pulsatile pump, injecting a fluid at various pressures ranging from about 7 mm Hg to about 25 mm Hg through the valve and into the pump, and then measuring the outflow from the pump in L/min at each preload pressure against a constant after load pressure of 90 mm Hg. The single pulsatile pump is set to eject automatically when it becomes fully filled. Accordingly, the output is a measure of the inflow through the valve. Pumps comprising a stiff valve as compared to a pliable valve have a decreased output at each pressure. It is believed that the decrease in output for pumps comprising a stiff valve results either from a decrease in the diameter of the orifice of the stiffer valve and thus a reduced flow into the pump and/or from an incomplete closure of the stiffer valve during pump ejection.

Prior to treatment in accordance with the method, the valve, which had been stored in 0.2% stabilized glutaraldehyde was placed at the inflow port of the pump and the output of the pump in L/min at various input pressures was measured. It was then removed from the pump, immersed in the glycerol-containing solution, air-dried at a relative humidity of 10 to 30% for 24 hours, sterilized by exposure to ethylene oxide at 54–57° C. for 130 minutes, and rehydrated in physiologic saline. It was then placed back into the inflow port of the pump and the output at various input pressures was determined. The results are shown in FIG. 2.

Figure 2:
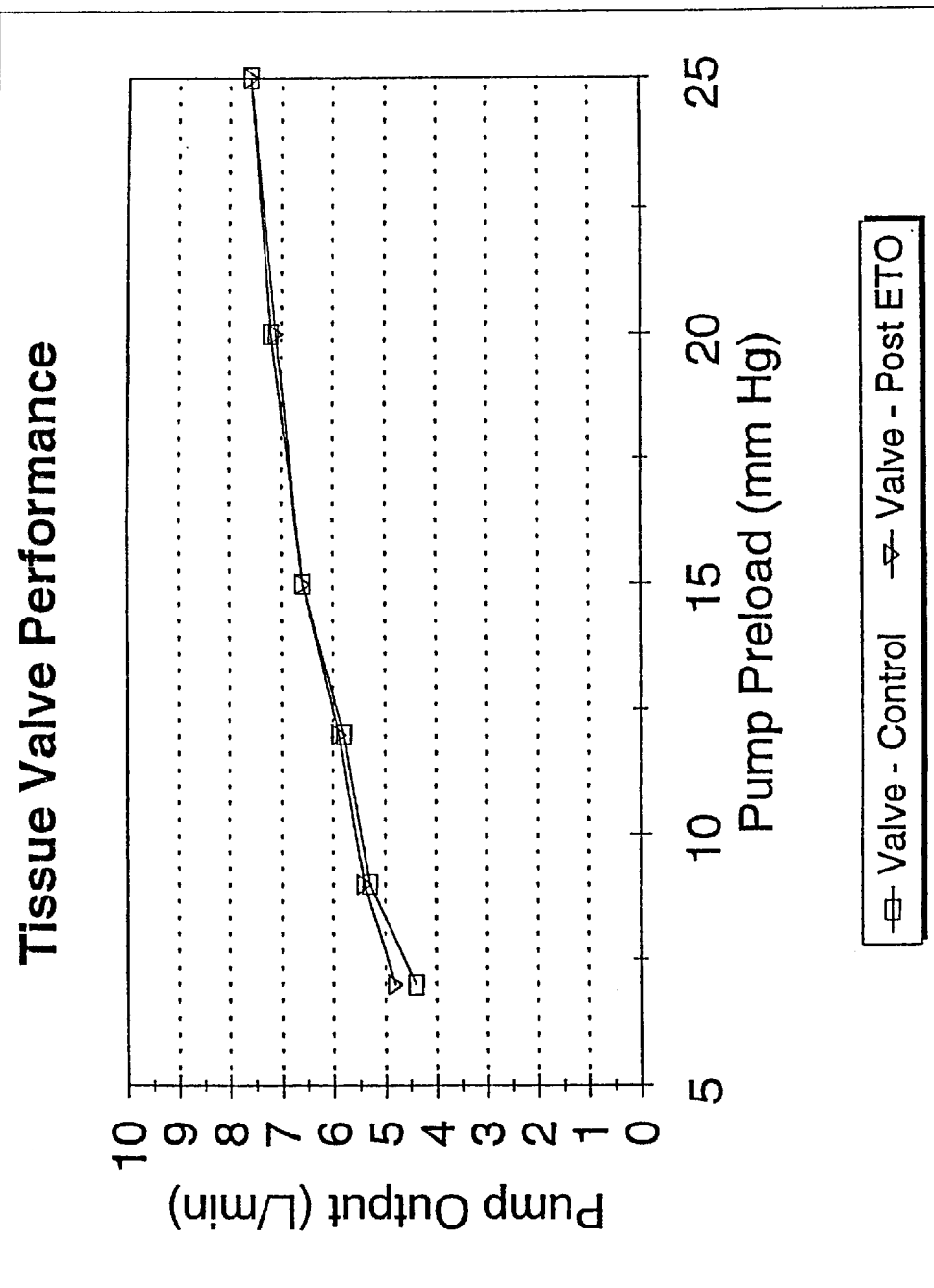
FIG. 2 is a graph comparing the performance of a porcine valve before and after treatment in accordance with the present method.

As shown in FIG. 2, the pump containing a valve that had been treated in accordance with the present method and stored in ambient air for 2 weeks did not exhibit a decreased output at any preload pressure from about 7 mm Hg to 25 mm Hg. Thus, the output of the pump comprising a valve treated in accordance with the present method was nearly identical to a pump comprising a valve that had been stored in 0.2% stabilized glutaraldehyde.

EXAMPLE 5

Single Cycle Dimensional Stabilization and Storage of Bovine Pericardium

A 2×1 cm specimen of bovine pericardial tissue, cross-linked with glutaraldehyde, was rinsed with de-ionized water to remove the glutaraldehyde. The tissue was then treated in a 57% glycerol/water solution for two hours after three times of rinsing with the same solution. Thereafter, the treated tissue was air dried at room temperature and 25% relative humidity for 4 hours. The dry tissue was cut into two 1×1 cm pieces. Each piece was placed in a petri disk and then sealed in a SURGICOT VIS-U-ALL-II sterilization bag. One sample, labeled as DPTS011800 E010, was a control, and was not subjected to ETO gas sterilization. One sample, labeled as DPTS011800 NC 01, was sterilized by ETO gas. Thereafter, both treated, fixed tissue samples were stored for seven days at standard temperature and relative humidity prior to sterility testing. Routine bacterial culture (i.e., evaluation of growth of gram negative bacilli in thioglycollate broth exposed to the tissue samples) showed a positive result in bacterial growth for the control sample not subjected to ETO gas sterilization. No bacterial growth was observed for the ETO gas sterilized sample.

What is claimed is:

1. A method of preparing a tissue component for dry storage, comprising the following steps:
    (a) providing an animal tissue component, said tissue component having an aqueous fluid within the interstices thereof;
    (b) treating said tissue component with an aqueous treatment solution comprising a dimensional stabilizer for a time sufficient to allow said aqueous treatment solution to equilibrate with the aqueous fluid contained within the interstices of the tissue component, said dimensional stabilizer being a biocompatible, organic compound comprising a plurality of carbon atoms and a plurality of hydroxyl groups, each of said plurality of hydroxyl groups being covalently bonded to a carbon atom;
    (c) removing said treated tissue component from the aqueous treatment solution; and
    (d) storing said treated tissue component in air in a container.

2. The method of claim 1 further comprising the step of sterilizing said tissue component by exposure to ethylene oxide gas or ionizing radiation either before or after placement in said container.

3. The method of claim 2 wherein the animal tissue component is fixed such that proteins in the animal tissue component have a reduced solubility, antigenicity and biodegrading properties as compared to proteins in a native tissue component.

4. The method of claim 2 wherein the volume of said aqueous treatment solution is at least 2 times the volume of the tissue component.

5. The method of claim 2 wherein said dimensional stabilizer is selected from the group consisting of a polyhydric alcohol, a derivative of a polyhydric alcohol, a water soluble carbohydrate, a water soluble gum, and combinations thereof.

6. The method of claim 2 wherein said dimensional stabilizer is a water-soluble polyhydric alcohol or a derivative thereof.

7. The method of claim 2 wherein said dimensional stabilizer is glycerol or a derivative thereof.

8. The method of claim 2 wherein the concentration of said dimensional stabilizer in said aqueous treatment solution is from about 30% to about 95% (v/v).

9. The method of claim 2 wherein the concentration of glycerol or a derivative thereof in said aqueous treatment solution is about 50% to about 70% v/v.

10. The method of claim 2 wherein said container is a gas permeable package.

11. The method of claim 2 wherein said tissue component is sterilized by a process comprising
   (a) placing said treated tissue component in a package;
   (b) sealing said package; and
   (c) exposing said package to ethylene oxide gas.

12. The method of claim 2 wherein the treated tissue component is stored in air at a relative humidity from about 10% to about 30%.

13. A method of preparing a chemically cross-linked tissue component for dry storage, comprising the following steps:
   (a) providing a chemically cross-linked tissue component, said tissue component having an aqueous fluid within the interstices thereof;
   (b) treating said chemically cross-linked tissue component with an aqueous treatment solution comprising a dimensional stabilizer for a time sufficient to allow said aqueous treatment solution to equilibrate with the aqueous fluid contained within the interstices of the chemically cross-linked biological material, said dimensional stabilizer being a biocompatible, organic compound comprising a plurality of carbon atoms and a plurality of hydroxyl groups, each of said plurality of hydroxyl group being covalently bonded to a carbon atom, wherein the concentration of the dimensional stabilizer in said aqueous treatment solution is from about 30% to about 95% v/v;
   (c) providing a sealable package having a chamber and comprising a member having an inner surface which defines at least a portion of said chamber, said chamber comprising air, said member comprising a gas permeable membrane;
   (d) removing said treated chemically cross-linked tissue component from said aqueous treatment solution and placing said tissue component in the chamber of said package, and
   (e) storing said tissue component in air in said package.

14. The method of claim 13 further comprising the step of sterilizing said tissue component by exposure to ethylene oxide gas or ionizing radiation either before or after placement in said gas permeable package.

15. The method of claim 14 wherein said treated chemically cross-linked tissue component is stored in said package for a period of at least four hours.

16. The method of claim 14 wherein said treated chemically cross-linked tissue component is stored in air at a relative humidity from about 10% to about 30%.

17. A method of preparing a packaged chemically cross-linked tissue component for dry storage, comprising the following steps:
   (a) providing a chemically cross-linked tissue component said tissue component having an aqueous fluid within the interstices thereof;
   (b) dimensionally stabilizing the chemically cross-linked tissue component by a process comprising: treating said chemically cross-linked tissue component with an aqueous treatment solution comprising a dimensional stabilizer for a time sufficient to allow said aqueous treatment solution to equilibrate with the aqueous fluid contained within the interstices of the chemically cross-linked tissue component;
   (c) removing said dimensionally-stabilized, chemically cross-linked tissue component from said aqueous treatment solution;
   (d) drying said dimensionally-stabilized, chemically cross-linked tissue component in air;
   (e) placing said dimensionally stabilized, chemically cross-linked tissue component in a gas permeable package having a chamber that comprises air, wherein said tissue component is placed in said gas permeable package prior to or after drying; and
   (f) storing said dimensionally-stabilized, chemically cross-linked tissue component in air in said gas permeable package for a period of at least 4 hours.

18. The method of claim 17 further comprising the step of sterilizing said treated chemically cross-linked tissue component by gas sterilization or by ionizing radiation either before or after placement in said gas permeable package.

19. The method of claim 18 wherein the dimensionally-stabilized, chemically cross-linked tissue component is stored in air at a relative humidity from about 10% to about 30%.

20. A method of preparing an animal tissue component for dry storage, comprising the following steps:
   (a) providing an animal tissue component, said tissue component having an aqueous fluid within the interstices thereof;
   (b) immersing said tissue component in an aqueous treatment solution comprising a dimensional stabilizer, where the volume of the aqueous treatment solution is at least two times the volume of the tissue component;
   (c) providing a sealable gas permeable package having a chamber and comprising a member having an inner surface which defines at least a portion of said chamber, said chamber being essentially free of liquid and comprising air, said member comprising a gas permeable membrane;
   (d) removing said treated tissue component from said aqueous treatment solution and placing said treated tissue component in the chamber of said package; and
   (e) storing said treated tissue component in air in said package for a period of at least four hours.

21. The method of claim 20 further comprising the step of sterilizing said treated tissue component by exposure to ethylene oxide gas or ionizing radiation either before or after placement in said gas permeable package.

22. The method of claim 21 wherein proteins in the animal tissue component are chemically cross-linked.

23. The method of claim 21 wherein said dimensional stabilizer is glycerol or a derivative thereof and wherein the concentration of said dimensional stabilizer in said aqueous treatment solution is from about 30% to about 95% (v/v).

24. The method of claim 21 wherein the concentration of said glycerol or derivative thereof is about 50% to about 70% (v/v).

25. A method of preparing a bioprosthetic device comprising a chemically cross-linked tissue component for implantation in a patient, comprising the steps of:
   (a) providing a packaged bioprosthetic device, comprising:

i) a gas permeable package having a closed chamber and comprising a member having an inner surface which defines at least a portion of said chamber, said chamber being essentially free of liquid, said member comprising a gas permeable membrane; and ii) a bioprosthetic device comprising a chemically cross-linked tissue component contained within the chamber of said gas permeable package; wherein said tissue component comprises within the interstices thereof a dimensional stabilizer, said dimensional stabilizer being a biocompatible, organic compound comprising a plurality of carbon atoms and a plurality of hydroxyl groups, each of said plurality of hydroxyl group being covalently bonded to a carbon atom;

(b) removing said bioprosthetic device from said package;

(c) rehydrating said tissue component in an aqueous solution.

26. The method of claim 25 wherein the dimensional stabilizer is selected from the group consisting of a polyhydric alcohol, a derivative of a polyhydric alcohol, a water soluble carbohydrate, a water soluble gum, and combinations thereof.

27. The method of claim 3 wherein the proteins of said tissue component are chemically cross-linked.

28. The method of claim 17 wherein said tissue is dried in air at a temperature of 15° C. or greater.

* * * * *